United States Patent
Dash

(10) Patent No.: US 7,792,779 B2
(45) Date of Patent: Sep. 7, 2010

(54) DETECTION OF EPIDEMIC OUTBREAKS WITH PERSISTENT CAUSAL-CHAIN DYNAMIC BAYESIAN NETWORKS

(75) Inventor: Denver Dash, Pittsburgh, PA (US)

(73) Assignee: Intel Corporation, Santa Clara, CA (US)

( * ) Notice: Subject to any disclaimer, the term of this patent is extended or adjusted under 35 U.S.C. 154(b) by 694 days.

(21) Appl. No.: 11/806,996

(22) Filed: Jun. 5, 2007

(65) Prior Publication Data

US 2008/0306896 A1 Dec. 11, 2008

(51) Int. Cl.
- *G06F 9/44* (2006.01)
- *G06F 11/00* (2006.01)
- *G06F 12/14* (2006.01)
- *G06F 12/16* (2006.01)
- *G06N 7/02* (2006.01)
- *G06N 7/06* (2006.01)
- *G08B 23/00* (2006.01)

(52) U.S. Cl. .......................... 706/52; 726/23
(58) Field of Classification Search ................... 706/52; 726/23

See application file for complete search history.

(56) References Cited

U.S. PATENT DOCUMENTS

| | | | |
|---|---|---|---|
| 2006/0095963 A1 | 5/2006 | Crosby et al. | |
| 2007/0005753 A1 | 1/2007 | Crosby et al. | |
| 2007/0083928 A1* | 4/2007 | Mattsson et al. | ............... 726/22 |
| 2008/0010225 A1* | 1/2008 | Gonsalves et al. | ............ 706/11 |

OTHER PUBLICATIONS

Ghahramani, Zoubin "Learning Dynamic Bayesian Networks" Adaptive Processing of Sequences and Data Structures vol. 1387 1998. Downloaded off of Springerlinke on Apr. 5, 2010.*

Pearl. Judea "Probabilistic Reasoning in Intelligent Systems; Networks of Plausible Inference" (2nd edition). San Francisco: Morgan Kaufmann Publishers, Inc.(1988) pp. 169-175.

Denver Dash, Branislav Kveton, John Mark Agosta, Eve M. Schooler. Jaideep Chandrashekar, Abraham Bachrach. and Alex Newman "When Gossip is Good: Distributed Probabilistic Inference for Detection of Slow Network Intrusions" In Proceedings of The Twenty-First National Conference on Artificial Intelligence. Boston, MA, Jul. 2006.

* cited by examiner

*Primary Examiner*—Donald Sparks
*Assistant Examiner*—Ben M Rifkin
(74) *Attorney, Agent, or Firm*—Pearl Cohen Zedek Latzer, LLP

(57) ABSTRACT

A method for determining a probability of a hidden variable from an observed variable in a Dynamic Bayesian Network is presented. The method includes identifying the network based on predetermined criteria, determining a number of hidden variables in a time slice of the network, determining a number of the time slices of the network, and determining the probability of the hidden variable from the observed variable in less than exponential time with respect to the number of hidden variables.

12 Claims, 4 Drawing Sheets

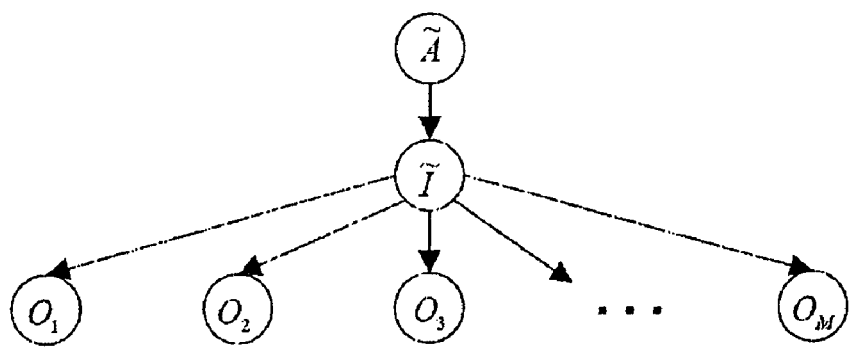

FIGURE 4

| $j_A$ | $j_I$ | $P(O) =$ | | | | | |
|---|---|---|---|---|---|---|---|
| 0 | 0 | $AAAIII:$ | $\{P_A$ | $[P_I$ | $\Sigma_o^0\}$ | $\sigma_I^0$ | |
| | 1 | $AAA\overline{I}II:$ | | $+P_{\overline{I}}P_I$ | $\Sigma_o^1\}$ | $\sigma_I^1$ | $\Sigma_I^0$ |
| | 2 | $AAA\overline{II}I:$ | | $+P_{\overline{I}}^2 P_I$ | $\Sigma_o^2\}$ | $\sigma_I^2$ | |
| | 3 | $AAA\overline{III}:$ | | $+P_{\overline{I}}^3$ | $\Sigma_o^3]\}$ | $\bar\sigma_I^0$ | |
| 1 | 0 | $\overline{A}AAIII:$ | $+P_{\overline{A}}P_A$ | $[\overline{P}_I$ | $\Sigma_o^0\}$ | $\overline\sigma_I^1$ | |
| | 1 | $\overline{A}AA\overline{I}II:$ | | $+\overline{P}_{\overline{I}}P_I$ | $\Sigma_o^1\}$ | $\sigma_I^1$ | $\Sigma_I^1$ |
| | 2 | $\overline{A}AA\overline{II}I:$ | | $+\overline{P}_{\overline{I}}P_{\overline{I}}P_I$ | $\Sigma_o^2\}$ | $\sigma_I^2$ | |
| | 3 | $\overline{A}AA\overline{III}:$ | | $+\overline{P}_{\overline{I}}P_{\overline{I}}^2$ | $\Sigma_o^3]\}$ | $\bar\sigma_I^1$ | |
| 2 | 0 | $\overline{AA}AIII:$ | $+P_{\overline{A}}^2 P_A$ | $[\overline{P}_I$ | $\Sigma_o^0\}$ | $\overline\sigma_I^2$ | |
| | 1 | $\overline{AA}A\overline{I}II:$ | | $+\overline{P}_{\overline{I}}\overline{P}_I$ | $\Sigma_o^1\}$ | $\sigma_I^2$ | $\Sigma_I^2$ |
| | 2 | $\overline{AA}A\overline{II}I:$ | | $+\overline{P}_{\overline{I}}^2 P_I$ | $\Sigma_o^2\}$ | $\sigma_I^2$ | |
| | 3 | $\overline{AA}A\overline{III}:$ | | $+\overline{P}_{\overline{I}}^2 P_{\overline{I}}$ | $\Sigma_o^3]\}$ | $\bar\sigma_I^2$ | |
| 3 | 0 | $\overline{AAA}III:$ | $+P_{\overline{A}}^3$ | $[\overline{P}_I$ | $\Sigma_o^0\}$ | $\overline\sigma_I^3$ | |
| | 1 | $\overline{AAA}\overline{I}II:$ | | $+\overline{P}_{\overline{I}}\overline{P}_I$ | $\Sigma_o^1\}$ | $\sigma_I^3$ | $\Sigma_I^3$ |
| | 2 | $\overline{AAA}\overline{II}I:$ | | $+\overline{P}_{\overline{I}}^2 P_I$ | $\Sigma_o^2\}$ | $\sigma_I^3$ | |
| | 3 | $\overline{AAA}\overline{III}:$ | | $+\overline{P}_{\overline{I}}^3$ | $\Sigma_o^3]\}$ | $\bar\sigma_I^3$ | |

FIGURE 5

DETECTION OF EPIDEMIC OUTBREAKS WITH PERSISTENT CAUSAL-CHAIN DYNAMIC BAYESIAN NETWORKS

BACKGROUND OF THE INVENTION

1. Field of the Invention

The present invention relates to detection of epidemic outbreaks in a large population of hosts. In particular, the present invention relates to detection of an epidemic outbreak by making use of a particular type of Dynamic Bayesian Network which is defined herein as a Persistent Causal-Chain Dynamic Bayesian Network (PCCDBN).

2. Description of the Prior Art

A Bayesian Network is a type of Directed Acyclic Graph which is used to show causal relationships between random variables. A Directed Graph contains a set of nodes and a set of arrows describing a path from node to node. A node X is said to be a parent of another node Y if there is an arrow from X to Y. A Directed Acyclic Graph is a special type of Directed Graph in which there is no directed path from a node back to itself.

In a Bayesian Network, the nodes represent random variables and the arrows represent the fact that the child node may be conditionally dependent on the parent. The random variables may take on a discrete value such as true or false or a continuous value such as one of the real numbers.

In a Bayesian Network, for any node X the conditional probability that the random variable X takes on any particular value, given the value of all of X's parents is specified. Given these conditional probabilities, it is then possible to calculate the probability that an event occurred given other events occurring. This process is known as inference.

In a Bayesian Network, nodes are either hidden or observed. A hidden node, as opposed to an observed node, is a node whose value is not known. A node may be explicitly represented in the model but still hidden due to a lack of observable information. A random variable may also be hidden due to a lack of known conditional independencies, and thus not be represented by a node in the Bayesian network.

A Dynamic Bayesian Network (DBN) extends the concept of the Bayesian Network into the time dimension. In a Dynamic Bayesian Network, the Bayesian Network is repeated throughout time. Just as arrows create causal connections between nodes in a Bayesian Network, allows are used in a Dynamic Bayesian Network to causally link the network at one time instance to the network at the next time instance.

When a Dynamic Bayesian Network uses discrete random variables, it may be computationally intractable to solve for the conditional probabilities among nodes. Standard approaches using exact inference models require exponential time due to the large number of cross-temporal dependencies that exist between nodes. Such an exponential approach is intractable and cannot be solved in real time. Other inference models have been developed to solve the network in less than exponential time, however these approaches introduce approximations and cannot give exact solutions.

Thus, it would be beneficial to have an exact inference model that could solve a type of discrete Dynamic Bayesian Network in less than exponential time by taking advantage of certain properties of the network.

BRIEF DESCRIPTION OF THE DRAWINGS

Embodiments of the invention will be understood and appreciated more fully from the following detailed description in conjunction with the drawings in which like reference numerals indicate corresponding, analogous or similar elements, and in which:

FIG. 4 shows an embodiment of a Persistent Causal Chain Dynamic Bayesian Network representation of the Dynamic Bayesian Network of FIG. 1;

FIG. 5 shows an embodiment of how P(O) is calculated in the network represented in FIG. 4.

DESCRIPTION OF THE PREFERRED EMBODIMENT

In the following description, various aspects of the present invention will be described. For purposes of explanation, specific configurations and details are set forth in order to provide a thorough understanding of the present invention. However, it will be apparent to one skilled in the art that the present invention may be practiced without the specific details presented herein. Furthermore, well-known features may be omitted or simplified in order not to obscure the present invention. Various examples are given throughout this description. These are merely descriptions of specific embodiments of the invention. The scope of the invention is not limited to the examples given.

Unless specifically stated otherwise, as apparent from the following discussions, it is appreciated that throughout the specification, discussions utilizing terms such as "processing," "computing," "calculating," "determining," or the like, refer to the action and/or processes of a processor, computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

The processes and displays presented herein are not inherently related to any particular computer, communication device or other apparatus. The desired structure for a variety of these systems will appear from the description below. In addition, embodiments of the present invention are not described with reference to any particular programming language, machine code, etc. It will be appreciated that a variety of programming languages, machine codes, etc. may be used to implement the teachings of the invention as described herein.

Embodiments of the present invention may include apparatus for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, magnetic-optical disks, read-only memories, compact disc read-only memories, random access memories, electrically programmable read-only memories, electrically erasable and programmable read only memories, magnetic or optical cards, or any other type of media suitable for storing electronic instructions, and capable of being coupled to a computer system bus.

Figure 1:
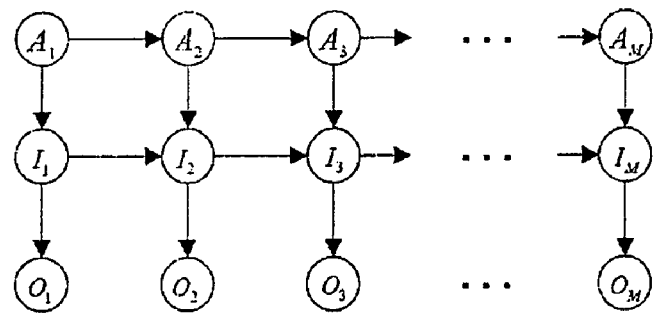
FIG. 1 shows an embodiment of a Dynamic Bayesian Network with a time horizon of length M.

An embodiment of a Dynamic Bayesian Network with a time horizon of length M is shown in FIG. 1. In an embodiment of the invention this network may represent a single host under attack. A host may be any computing device that provides a service. Thus, a host may be a personal computer, a file server, a cell phone, a data base system, a web server or the like. An attack may be a malicious attempt to take over or interrupt the normal operation of the host. Thus, an attack may be a virus, a worm, a Trojan horse, a denial of service or the like. In another embodiment of the invention, the network may represent a catastrophic system failure such as a power outage, an assembly line stoppage, or the like.

In the DBN of FIG. 1, the root cause node $A_i$ may represent a binary random variable that indicates whether an attack has taken place against the host at time instance i. The node $I_i$ may represent a binary random variable that indicates whether the host has been infected at time instance i. The node $O_i$ may represent a binary random variable that indicates the presence or absence of some observable symptom in the host at time instance i. Within a time instance i, an arrow connects $A_i$ to $I_i$ and an allow connects $I_i$ to $O_i$. This is known as an instantaneous causal chain. The term "instantaneous causal chain" is defined below. Thus, there may be a chain of conditional probabilities linking an attack occurring on the host, an infection occurring on the host given the host is attacked and an observation occurring of a symptom of the host given the host is infected. Such a network may be used to discover whether a host is under attack or whether a host is infected using observations of symptoms within a host. In other words, observable node $O_i$ may be used to determine information about hidden nodes $I_i$ and $A_i$.

Between time instances i and i+1, an allow connects $A_i$ to $A_{i+1}$ and an arrow connects $I_i$ to $I_{i+1}$. It is a reasonable assumption that a host that is under attack will remain under attack. Similarly, it is a reasonable assumption that a host that is infected will remain infected. Thus, for all i, if $A_i$ is true then $A_{i+1}$ is also true and if $I_i$ is true then $I_{i+1}$ is also true. In other words, the conditional probability of $A_{i+1}$ occurring given that $A_i$ has occurred or $I_{i+1}$ occurring given that $I_i$ has occurred is 100%. This quality is known as persistence. The term "persistence" is defined below. If a Dynamic Bayesian Network has instantaneous causal chains and exhibits the quality of persistence it is known as a Persistent Causal Chain Dynamic Bayesian Network (PCCDBN).

Figure 2:
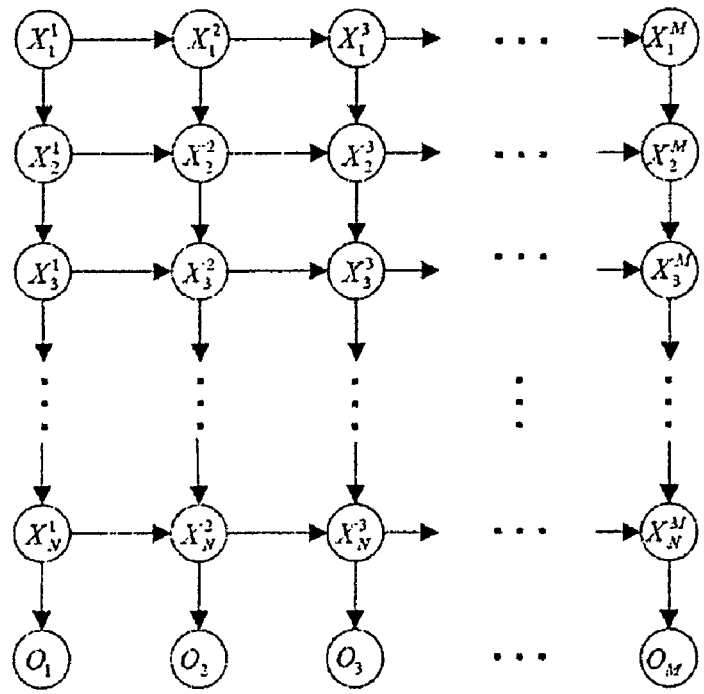
FIG. 2 shows an embodiment of a Dynamic Bayesian Network with a causal chain of length N and a time horizon of length M.

To more rigorously define a Persistent Causal Chain Bayesian Network, an embodiment of a more generalized Dynamic Bayesian Network with a causal chain of length N and a time horizon of length M is shown in FIG. 2. A Dynamic Bayesian Network is a PCCDBN if it meets the following criteria:

1) Each time slice j contains an instantaneous causal chain:

$$X_1^j \to X_2^j \to \ldots \to X_N^j \to O_j$$

where $X_i^j$ is a binary hidden random variable for i, j and $O_j$ is a single binary observed random variable.

2) Each state variable $X_i^j$ exhibits persistence in its on state (the on state is defined as "1" and the off state is defined as "0"):

$$P(X_i^j=1|X_i^{j-1}=1, X_{i-1}^j=x)=1$$

For all $x \in \{0,1\}$ and for $2 \leq j \leq M, 2 \leq i \leq N$, and $$P(X_1^j=1|X_1^{j-1}=1)=1 \text{ for all } j>1$$

3) The conditional distribution of each variable given its parent set is independent of time:

$$P(X_i^j=1|X_i^{j-1}=0, X_{i-1}^j=1)=P_i,$$

$$P(X_i^j=1|X_i^{j-1}=0, X_{i-1}^j=0)=\overline{P}_i,$$

with boundary conditions $$P(X_1^1=1)=P(X_1^j=1|X_1^{j-1}=0)=P_1,$$

$$P(X_i^1=1|X_{i-1}^1=1)=P_i,$$

$$P(X_i^1=1|X_{i-1}^1=0)=\overline{P}_i.$$

In Dynamic Bayesian Networks such as the network of FIG. 1, the standard method for performing inference is to group the hidden variables into a single state variable S={A, I}. Doing such converts the DBN into a standard Hidden Markov Model (HMM). Each variable A and I have two possible states 1 and 0 which may also be represented as true and false or on and off. Thus, each variable A and I have a state space n of size two. Such an HMM has a state space of size $n_S = n_A \times n_I = 2 \times 2 = 4$. Because the variables are binary and thus have two possible states it is mote convenient to define $n_S$ as equal to 2^(number of state variables in S).

Figure 3:
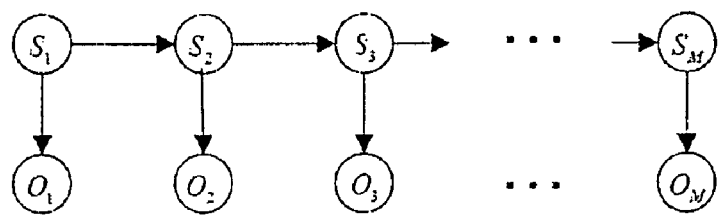
FIG. 3 shows an embodiment of a Hidden Markov Model representation of the Dynamic Bayesian Network of FIG. 1.

An embodiment of a Hidden Markov Model representation of a Dynamic Bayesian Network is shown in FIG. 3. Inference in this model may be performed in $O(n_S \cdot M)$ using belief propagation and/or the Viterbi algorithm. In order to convert the DBN of FIG. 2 into a Hidden Markov Model, state variable S may be defined as $\{X_1, X_2, \ldots, X_N\}$. Thus, $n_S$ would have a state space of $2^N$. As stated above, the size of the state space of $n_S$ grows exponentially with respect to the number of nodes in the causal chain, N. Thus, when a Hidden Markov Model of the network is used, the inference calculation grows exponentially as well and can be performed in $O(2^N \cdot M)$. Such exponential growth can quickly become computationally intractable.

The temporal dependence that is due strictly to persistence may lead to mole efficient inference. This is because persistence leads to a simpler inference model than general dependence would normally require. For example, persistence reduces the number of allowed configurations of $\{A_1, A_2, \ldots, A_M\}$ and $\{I_1, I_2, \ldots, I_M\}$ from $2^M$ to M+1. Instead of having M variables each with 2 possible states ($2^M$ configurations), persistence allows for only M+1 configurations because of the assumption that once a variable is "on" it stays on. Thus, if M is 3 there are only the following 4 configurations: {0, 0, 0}, {0, 0, 1}, {0, 1, 1}, and {1, 1, 1}. The first configuration represents the variable never turning on, whereas the last configuration represents the variable turning on immediately.

Perhaps the simplest way to exploit persistence is to rewrite the model in FIG. 3 to an embodiment of a Persistent Causal Chain Dynamic Bayesian Network as shown in FIG. 4. Two new variables are defined in FIG. 4, Ã and Ĩ, denoting the time at which A and I become true, respectively. Thus, the effective size of the "state space" in this model is O(M) (where "state space" refers to the number of states of variables $\tilde{A}$ and $\tilde{I}$). Standard exact inference models such as belief propagation may be performed on this model in $O(M^2 \cdot N)$. Reorganizing the model in this way removes the exponential dependence on N, but the calculation is now quadratic in M. In typical DBN applications it may be beneficial to let M grow indefinitely. A quadratic dependence on M may make the calculations quickly become intractable which may not be an ideal solution.

There may be more structure in the inference calculation above than is captured in the model of FIG. 4. To illustrate this structure, a sketch detailing an embodiment of how to calculate P(O) for the model of FIG. 4 is shown in FIG. 5. In calculating P(O), it may be necessary to marginalize out all the combinations of hidden states, so this calculation can serve as a crucible of sorts for any inference queries that one would want to ask about the network.

FIG. 5 presents this calculation in a notation that mirrors the notation that will be used later in a more generalized proof. Here $P_I$ is used to denote the probability of I firing (turning on, being set to true, changing to 1) given that A has fired, i.e. the true-positive probability. $\overline{P}_I$ is used to denote the probability of I firing given that A has not fired, i.e. the false-positive probability. Both probabilities assume that I has not filed previously. For conciseness of notation, $P_{\bar{I}}$ and $\overline{P}_{\bar{I}}$ are also defined to be the complements of $P_I$ and $\overline{P}_I$, respectively. Similarly, $P_A$ and $\overline{P}_A$ are used to denote the probability of A filing or not, respectively. Because A does not have any parent nodes, there is no need for $P_{\bar{A}}$ and $\overline{P}_{\bar{A}}$ notation. In the general notation below, $\overline{P}_{\bar{i}}$, etc. will be used to denote the conditional probabilities for variable $X_i$ given variable $X_{i-1}$.

The possible configurations of A's and I's through time are indexed by the variables $j_A$ and $j_I$, respectively. Because of persistence, there are only O(M) values of each of these in general. In the present example $j_A \in \{0,1,2,3\}$ corresponds to $\{AAA, \overline{A}AA, \overline{AA}A, \overline{AAA}\}$, respectively, and similarly for $j_I$. For this notation, AAA means that A fires immediately (configuration 0) and $\overline{AAA}$ means that A does not fire (configuration 3). These variables have a natural semantics: $j_I$ denotes the latest time slice in which I fails to fire. Finally, $$\sum_{O}^{j_I}$$

denotes the probability of all observed nodes given that the I variables are in configuration $j_I$.

$$\sum_{O}^{j_I} = \prod_{i=1}^{M} P(O_i = o_i \mid I_i = \delta(i > j_I)),$$

where $\delta(x) = 1$ if and only if $x$ is true.

An important notational point is evident here: in FIG. 5 many $P_{\bar{I}}$, etc., variables are raised to a power. These powers are easily confused with superscripts that are also frequently used in this application. Thus, care has been taken to ensure that only P's will be raised to powers and no P's will have superscript indices.

To better clarify the notation, row $j_A$ equals 1 is explained below. As explained above, $j_A$ equals 1 denotes the configuration in which A does not fire in time instance 0 and instead files (and stays true) at time instance 1. For every configuration of $j_A$ there are four configurations of $j_I$. Namely, I fires at time instance 0, 1, 2 or not at all. As with A firing, if I fires at time instance x, it does not fire before time instance x and remains true for all time instances after x. The probability for A not firing at time instance 0 and then firing at time instance 1 is equal to $P_{\bar{A}} P_A$. Thus, this portion of P(O) in which $j_A$ equals 1 will have $P_{\bar{A}} P_A$ as a multiplicative factor for all configurations of $j_I$ within the row. For the configuration $\overline{A}AAI I I$, I fires before A, thus this portion of P(O) is equal to the multiplicative factor $P_{\bar{A}} P_A$ multiplied by $\overline{P}_I$ (probability of I firing before A) times $$\sum_{O}^{0}$$

(probability of all observed nodes given that I is in configuration 0; I fires immediately in time instance 0). This process may be repeated for all $j_A$ and $j_I$ using similar reasoning.

Figure 6:
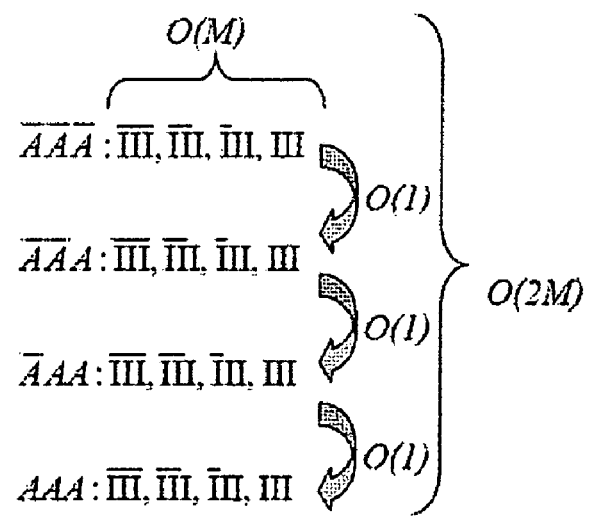
FIG. 6 shows an embodiment of how linear-time inference can be performed on the network represented in FIG. 4.

FIG. 6 shows an embodiment of how linear-time inference can be performed on the network represented in FIG. 4. All the terms necessary for $j_A = 0$ may be calculated in O(M) time. Once these terms are calculated, all the remaining terms may be calculated by making M constant time moves. This may be accomplished by partitioning all the terms for each value of $j_A$ into the $\sigma_I^{j_A}, \overline{\sigma}_I^{j_A}$, and $\hat{\sigma}_I^{j_A}$ terms shown in FIG. 5. For a given configuration, a term may be partitioned into $\sigma_I^{j_A}$ if I fires at the same time or after A fires. A term may be partitioned into $\overline{\sigma}_I^{j_A}$ if I fires before A files. Lastly, a term may be partitioned into $\hat{\sigma}_I^{j_A}$ if I never fires. Recursion relations may then be derived relating $\sigma_I^j$ to $\sigma_I^{j+1}$, $\overline{\sigma}_I^j$ to $\overline{\sigma}_I^{j+1}$, and $\hat{\sigma}_I^j$ to $\hat{\sigma}_I^{j+1}$. The details of these recursion relations are given below. While calculating the various $\sigma_I^{j_A}, \overline{\sigma}_I^{j_A}$, and $\hat{\sigma}_I^{j_A}$ terms the $$\sum_{I}^{j_A}$$

terms may also be calculated since they are just the sum of the various $\sigma_I^{j_A}, \overline{\sigma}_I^{j_A}$, and $\hat{\sigma}_I^{j_A}$ terms. If there were more than two variables in the causal chain (for example, in the network of FIG. 2), then this calculation may be recursed by associating $$\sum_{I}^{j_A}$$

with $$\sum_{O}^{j_I}$$

and $P_I$ with $P_A$, etc., N times to give a total complexity of O(N M).

It is useful to return to the network of FIG. 2 in order to prove this result more generally. For uniformity of notation, $\overline{P}_A = P_I$. M denotes the number of time steps being considered by the model. There is assumed to be an instantaneous causal chain of length N hidden variables, each terminating with a single observation O. The phrase "$X_i^j$ has filed" is used to indicate that $X_i^j = 1$.

A common shorthand notation $X_{i:j}^{j:k}$ is used to denote the set of variables:

$$X_{i:l}^{j:k} = \begin{Bmatrix} X_i^j & X_i^{j+1} & \cdots & X_i^k \\ X_{i+1}^j & X_{i+1}^{j+1} & \cdots & X_{i+1}^k \\ \vdots & \vdots & \vdots & \vdots \\ X_l^j & X_l^{j+1} & \cdots & X_l^k \end{Bmatrix}$$

The notation $X_i$ may be used to refer to an arbitrary member of $X_i^{1:M}$, or $X^j$ may be used to refer to an arbitrary member of $X_{1:N}^j$.

One version of the problem of calculating the value of one node from other nodes (known as the filtering problem) is to calculate the probability distribution of the unobserved state variables: $P(X_{1:N}^{1:M}|O_{1:M}=o_{1:M})$.

This quantity may be derived from the evidence (observed nodes) $P(O_{1:M}=o_{1:M})$ in a straightforward manner using Bayes' Rule and the Bayesian network joint factorization. Thus, calculating the evidence will be concentrated upon. Notational shorthand $P(O_{1:M})$ may be used to denote $P(O_{1:M}=o_{1:M})$ and similar abbreviations may be used for other probability statements.

The evidence can be expanded out as follows:

$$P(O_{1:M}) = \sum_{X_{1:N}^{1:M}} P(O_{1:M}|X_{1:N}^{1:M}) \cdot P(X_{1:N}^{1:M}) \quad \text{(EQ 1)}$$

The persistence assumption assigns zero probability to any configuration of $X_i^{1:M}$ such that $X_i^j=0$ when $X_i^{j'}=1$ for $j>j'$. Thus, there are only M+1 non-zero probability configurations of $X_i^{1:M}$ for each i, as illustrated above.

Let $\{j_i:0\leq j_i\leq M\}$ index the sequence of $X_i^{1:M}$ in which variable $X_i^{j_i}$ is the last (highest-time) variable to be in the off state, unless $j_i=0$ in which case it indexes the sequence in which all $X_i$ are in the on state. As an example, if M=3, then $j_i=\{0,1,2,3\}$ indexes the states $\{111, 011, 001, 000\}$, respectively. All configurations not indexed by $j_i$ have zero probability due to the persistence assumption (for example state 010). To simplify notation, $j_i$ is used to denote the event that $X_i^{1:M}$ is in the sequence indexed by $j_i$. Equation 1 can be decomposed according to the network structure as follows:

$$P(O_{1:M}) = \sum_{j_1=0}^{M} P(j_1) \sum_{j_2=0}^{M} P(j_2|j_1) \cdot \quad \text{(EQ 2)}$$
$$\sum_{j_3=0}^{M} P(j_3|j_2) \cdots \sum_{j_N=0}^{M} P(j_N|j_{N-1}) P(O_{1:M}|j_N)$$

Recall that $P_i$ is the probability that variable $X_i$ will fire for the first time given that its causal parent has fired, and $\overline{P}_i$ is the probability that $X_i$ will fire for the first time given that its causal parent has not fired:

$$P_i \equiv P(X_i^j=1|X_i^{j-1}=0, X_{i-1}^j=1), \quad \text{(EQ 3)}$$

and $$\overline{P}_i \equiv P(X_i^j=1|X_i^{j-1}=0, X_{i-1}^j=0). \quad \text{(EQ 4)}$$

Let $P_{\overline{i}}$ and $\overline{P}_{\overline{i}}$ denote the complements of $1-P_i$ and $1-\overline{P}_i$, respectively.

$\Sigma_k^L$ can be defined recursively to denote the $j_k$ sum from Equation 2 such that $j_{k-1}=L$:

$$\sum_k^L \equiv \sum_{j_k} P(j_k|j_{k-1}=L) \cdot \sum_{k+1}^{j_k} \quad \text{(EQ 5)}$$

with boundary condition $$\sum_{N+1}^{L} \equiv P(O_{1:M}|j_N = L)$$

The simplified example of FIG. 5 shows $$\sum_{I}^{j_A}$$

for all $j_A$ and with $$\sum_{N+1}^{L} \equiv P(O_{1:M}|j_N = L)$$

Using this notation, Equation 2 can be rewritten as:

$$\sum_{N+1}^{j_I} = \sum_{0}^{j_I}. \quad \text{(EQ 6)}$$

To clarify this notation, the above equations will be explained with reference to FIG. 5. In this case, N is equal to 2 since there are two hidden nodes A and I. M is equal to 3 and thus there are 4 configurations of each hidden node. Plugging into Equation 2, $$P(O_{1:3}) = \sum_{j_1=0}^{3} P(j_1) \sum_{j_2=0}^{3} P(j_2|j_1) \cdot P(O_{1:3}|j_2).$$

As explained above, $j_i$ indicates the state in which $X_i^{1:M}$ is in the sequence indexed by $j_i$. In FIG. 5 $j_1$ is associated with $j_A$ which indexes A and $j_2$ is associated with $j_1$ which indexes I. Thus, the equation can be rewritten as $$P(O_{1:3}) = \sum_{j_A=0}^{3} P(j_A) \sum_{j_I=0}^{3} P(j_I|j_A) P(O_{1:3}|j_I).$$

Considering only $j_A$ equals 0:

$P(j_A=0)*[P(j_1=0|j_A=0)*P(O_{1:3}|j_1=0)+P(j_1=1|j_A=0)*P(O_{1:3}|j_1=1)+P(j_1=2|j_A=0)*P(O_{1:3}|j_1=2)+P(j_1=3|j_A=0)*P(O_{1:3}|j_1=3)]$

If $P_{\overline{I}}$, $\overline{P}_{\overline{I}}$, $P_I$, $\overline{P}_I$, $P_A$, and $\overline{P}_A$ are plugged into the equation above, the resultant equation will match the first row ($j_A=0$) in FIG. 5.

Each $\Sigma_k^L$ can be partitioned as follows:

$$\Sigma_k^L = \bar{\sigma}_k^L + \sigma_k^L + \hat{\sigma}_k^L \quad \text{(EQ. 7)}$$

$\bar{\sigma}_k^L$ contains all the terms in the sum such that $X_k$ fires before $X_{k-1}$:

$$\bar{\sigma}_k^L = \sum_{j_k < L} \bar{P}_k^{L-j_k-1} \bar{P}_k \sum_{k+1}^{j_k}, \quad \text{(EQ 8)}$$

$\sigma_k^L$ contains all the terms in the sum such that $X_k$ fires at the same time as or after $X_{k-1}$:

$$\sigma_k^L = \sum_{L \leq j_k < M} \bar{P}_k^L P_k^{j_k - L} P_k \cdot \sum_{k+1}^{j_k}, \quad \text{(EQ 9)}$$

and $\hat{\sigma}_k^L$ contains all the terms in the sum such that $X_k$ never fires:

$$\hat{\sigma}_k^L = \sum_{L \leq j_k < M} \bar{P}_k^L P_k^{M-L} \cdot \sum_{k+1}^{M} \quad \text{(EQ 10)}$$

This partitioning matches the above partitioning in FIG. 5 into $\sigma_I^{jA}$, $\bar{\sigma}_I^{jA}$, and $\hat{\sigma}_I^{jA}$, and the terms here have similar definitions to the terms above.

In order to calculate Equation 6 in time O(M N), it is necessary to pre-compute $\bar{\sigma}_2^L$, $\sigma_2^L$, and $\hat{\sigma}_2^L$ for all values of L in O(M N).

As a boundary condition for the recursion, assume that $$\sum_{N+1}^{i}$$

has been calculated for all $0 \leq i \leq M$. It will be shown below how this is accomplished. It is also necessary to pre-calculate and cache $\bar{P}_l^i$ for $0 \leq l \leq N$ and $0 \leq i \leq M$, which can be done recursively in O(M N) time and space.

Given these initial quantities, one can calculate $\bar{\sigma}_N^i$ for $0 \leq i \leq M$ in O(M) time using the following recursion:

$$\bar{\sigma}_l^{i+1} = \bar{\sigma}_l^i + \bar{P}_l^i - \bar{P}_l - \sum_{l+1}^{i} \quad \text{(EQ 11)}$$

with boundary condition $\bar{\sigma}_N^0 = 0$.

One can calculate $\sigma_N^i$ for $0 \leq i \leq M$ in O(M) time using the following recursion:

$$\sigma_l^{i-1} = \frac{\sigma_l^i}{\bar{P}_l} P_l + \bar{P}_l^{i-1} - \bar{P}_l - \sum_{l+1}^{i-1} \quad \text{(EQ 12)}$$

with boundary condition $\sigma_N^M = 0$.

One can calculate $\hat{\sigma}_N^i$ for $0 \leq i \leq M$ in O(M) time using the following recursion:

$$\hat{\sigma}_l^{i-1} = \frac{\hat{\sigma}_l^j}{\bar{P}_l} P_l \quad \text{(EQ 13)}$$

with boundary condition $$\hat{\sigma}_N^M = \bar{P}_N^M - \sum_{N+1}^{M}.$$

Once $\bar{\sigma}_N^i$, $\sigma_N^i$, and $\hat{\sigma}_N^i$ are calculated, one can calculate all $\Sigma_N^i$ for $0 \leq i \leq M$ in O(M) time using Equation 7. Once $\Sigma_N^{0:M}$ is calculated, Equation 5 can be used to calculate $\Sigma_{N-1}^{0:M}$ in time O(M), and so on N times to get all values of $\Sigma_{1:N}^{0:M}$. Thus, the entire calculation takes O(M N) time.

In order to calculate $\Sigma_k^L$ in O(M) time it is necessary to compute $\Sigma_{N+1}^i$ (the probability of the observations for a given configuration i of $X_N^{1:M}$) for all $0 \leq i \leq M$ in O(M) time as well. Recall that $$\sum_{N+1}^{l} \equiv P(O_{1:M} \mid j_N = i).$$

Since the parents of each $O_j$ is given, for each i, this calculation is simply the product of the observations:

$$P(O_{1:M} \mid j_N = i) = \prod_{k=1}^{M} P(X_N^k, j_N = i) \quad \text{(EQ 14)}$$

Using existing notation, the following are defined:

$$P_{N+1} = P(O_k \mid X_N^k = 1), \quad \text{(EQ 15)}$$

$$\bar{P}_{N+1} = P(O_k \mid X_N^k = 0), \quad \text{(EQ 16)}$$

and with $P_{\overline{N+1}} = 1 - P_{N+1}$ and $\bar{P}_{\overline{N+1}} = 1 - \bar{P}_{N+1}$. Equation 14 can then be written as:

$$P(O_{1:M} \mid j_N = i) = \prod_{k=1}^{M} \phi_k^{\delta(k \leq i)} \cdot \bar{\phi}_k^{\delta(k > i)} \quad \text{(EQ 17)}$$

where $$\phi_k = \begin{cases} P_{N+1} & \text{if } O_i = 1 \\ P_{\overline{N+1}} & \text{otherwise} \end{cases}$$

and $$\bar{\phi}_k = \begin{cases} \bar{P}_{N+1} & \text{if } O_l = 1 \\ \bar{P}_{\overline{N+1}} & \text{otherwise} \end{cases}$$

Equation 17 can be calculated for all $0 \leq i \leq M$ in O(M) time via the recursion relation:

$$\sum_{N+1}^{0} = \prod_{k=1}^{M} \phi_i, \quad \text{(EQ 18)}$$

and $$\sum_{N+1}^{i+1} = \frac{\sum_{N+1}^{i}}{\bar{\phi}_i} \phi_i \quad \text{(EQ 19)}$$

FIG. 1 shows an embodiment of a PCCDBN that may be used for the detection of outbreaks in a population of $N_p$ hosts (the A nodes are shared among the $N_p$ hosts while each host has its own unique set of I nodes and O nodes). In an embodiment of the invention, the model may be used to detect a worm outbreak in a collection of networked devices. In other embodiments of the invention, a nearly identical model may be used to detect any contagious spread in any population as long as each member of the population is being monitored through time (by contrast, many disease surveillance applications for example sample a random subset of the population over time).

For detection with this model, at each time slice the quantity may be calculated:

$$\xi = \log P(A_M=1|O_{1:M}) - \log P(A_M=0:O_{1:M}), \quad (EQ\ 20)$$

which may have a threshold to determine if a global attack on the system is taking place.

This model differs significantly from prior art approaches. Most, if not all, time-series techniques for this task operate according to the model where some statistic(s) from the population is(are) sampled from the population at regular intervals, either by intentional periodic surveillance or by incidental measurements. Under this schema, the models that come closest to PCCDBN are HMM models. However, this model is novel for this task in that it may maintain a time-series of observations of each individual in the population and may use the model to merge those time-series in a principled manner. This added information qualitatively improves the ability to detect an outbreak.

Besides being novel in the way it monitors the population as well as being tractable for inference, the model in FIG. 1 may be very efficiently parallelized and distributed. Each local host $H_i$ may maintain its own observation history and calculate its own signal $\xi_i$. The aggregate signal for the entire population may be calculated by summing over all local signals (ignoring the prior): $\xi = \Sigma_i \xi_i$.

In a distributed setting, this may be implemented over a network by having hosts send messages containing their local $\xi_i$ values. Those $\xi_i$ values may be aggregated with other messages that the host has received to allow for exponential growth in the number of hosts that can participate in a given message, although the messages still can maintain a constant size. This technique may be prone to over-counting; although that may be mitigated by allowing messages to expire after a few hops and by ensuring that no host contributes to a message with the same originating host-time pair more than once.

EXAMPLE

The empirical setup for this model includes a system of noisy local detectors (LDs), which are noisy observable detectors sitting on the end-hosts. The LDs scan outgoing packets and count the number of UDP packets to unique destination IPs, itemized by source and destination port. The LDs may also scan memory used, CPU usage, and the like. PCCDBN inference was tested on five weeks of network traffic data for 37 hosts within a corporate enterprise network. In experiments where more than 37 hosts were used, the data was bootstrapped by uniformly-at-random selecting a starting-point for each virtual host at one of the original 37 host's data stream (original host again chosen uniformly-at-random).

Figure 7:
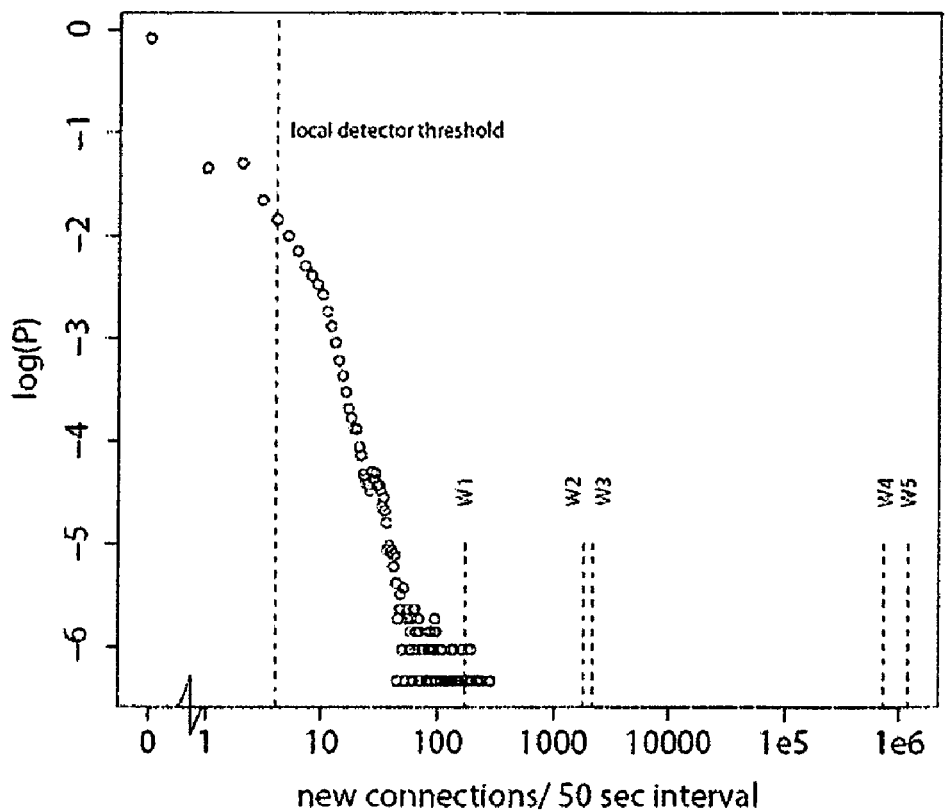
FIG. 7 shows a graph detailing noisy observations of outgoing packets on hosts in an experiment conducted on an embodiment of a Persistent Causal Chain Dynamic Bayesian Network (PCCDBN) designed to detect an epidemic outbreak.

FIG. 7 shows a graph detailing noisy observations of outgoing packets by the LDs aggregated over all machines for all five weeks. The LD was operated at a low threshold of 4 connections per 50 second intervals (shown as the vertical line in the figure). Thus, if the count is 4 or greater in time slice i, $O_i$ is set to 1.

This setup is designed to catch very slow worms that try to escape detection by sliding well under the background traffic, as seen by the relatively large histogram mass to the right of the LD threshold in FIG. 7. The lines in this plot labeled W1, W2, . . . , W5 show where some recent worm attacks would appear using this heuristic; the point being that this heuristic is very good for detection of fast worms, but for sneaky worms with slow propagation rate, this detector is very noisy, having a false positive rate on the order of thousands per week.

The simplicity of the LDs made simulating worm behavior on top of real network traffic trivial. A worm was modeled with two parameters: the spread rate S which indicated how many hosts the worm attempted to spread to per unit time, and the address density with which the worm was able to spread. For example, if the worm is randomly choosing addresses from the entire 32-bit address space and a network has 37 hosts, then the address density will be $37/2^{32}$. All results shown here use an S of 1 connection per 20 seconds, and set the address density to $1/1000$.

Simulations superimposed artificial worm traffic on the real enterprise traffic by releasing worms, letting the proportion of infected hosts grow to 1 in the population, then repeating 20 times. To test for false positive rates the enterprise traffic with no worm traffic superimposed was used. The results were averaged over all runs.

Very similar experiments were performed, where a Naive Bayes approximation to PCCDBNs was used for efficiency and was compared to several standard algorithms including a modified HMM and a Cumulative Sum (CUSUM) detector. Both the Naive-DBN and the modified HMM out-performed the rest of the tested models. The HMM model actually performed slightly better than the Naive-DBN model; however, the Naive Bayes DBN approximation performed qualitatively similarly and was much faster to run, so it was used it as the baseline in the experiments presented here.

The local detector false-positive rate $P(O_i=1|I_i=0)$ was estimated online using a Bayesian update assuming that all traffic was clean. After an outbreak, the parameters were reset to avoid having outbreak data inflate the assumed false positive rates. Each LD was allowed to maintain its own false positive and true positive rates independent of the other LDs. The true-positive rate $P(O_i=1|I_i=1)$ was fixed to a constant 0.95. The same method for estimating parameters was used for the Naive-DBN and the PCCDBN.

Regarding the state variables, it is assumed that:

$$P(I_i=1|I_{i-1}=0, A_i=1)=1/N_p \quad (EQ\ 22)$$

$$P(I_i=1|I_{i-1}=0, A_i=0)=0, \quad (EQ\ 23)$$

and that $$P(A_i=1|A_{i-1}=0)=0.001, \quad (EQ\ 24)$$

however, detection may be measured by sweeping through all detection thresholds, so the results are expected to be insensitive to the exact values of the priors if they are non-zero.

In the experiments here, three separate models are compared: the distributed Naive-DBN approximation and the PCCDBN model in both centralized form (C-PCCDBN), where all hosts report to a single detector every 10 seconds, and a distributed model (D-PCCDBN) where each host sent out 1 message every 10 seconds to a random other host. Messages were aggregated and given a time-to-live of 4 hops.

Figure 8:
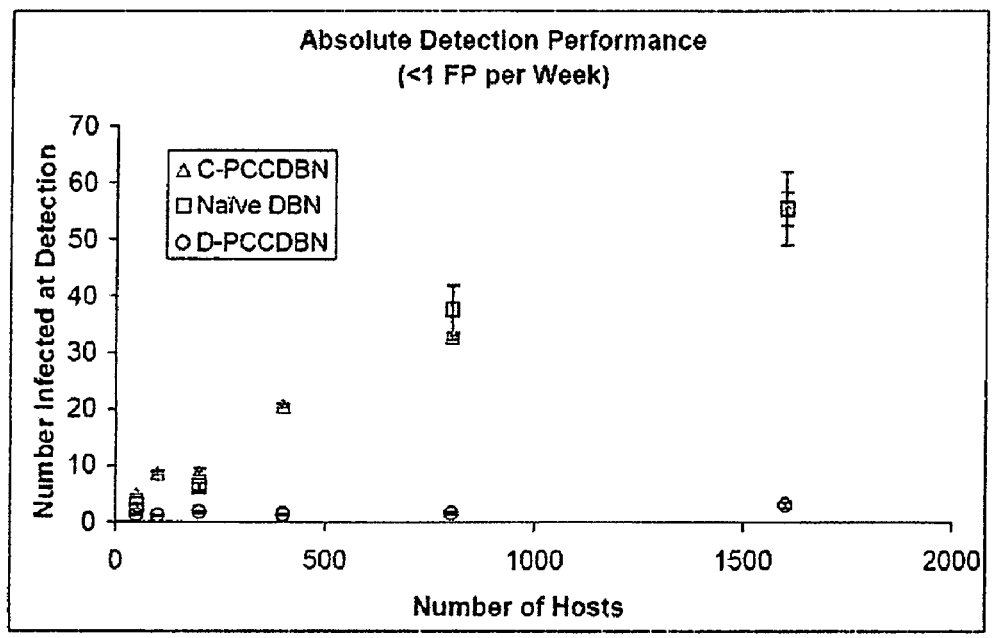
FIG. 8 shows a graph of the absolute detection performance of embodiments of a Naïve DBN model, a Centralized PCCDBN (C-PCCDBN) model, and a Distributed PCCDBN (D-PCCDBN) model.

The number of hosts was varied over the set $N_p \in \{50, 100, 200, 400, 800, 1600\}$. The results are shown in FIG. 8

These results are striking for at least two reasons. First, they show that an embodiment of D-PCCDBN possesses qualitatively different detection ability than either of the other two models (and all the models tested previously for that matter). Namely, D-PCCDBN made a detection when roughly a fixed absolute value of hosts was infected, as opposed to when a fixed percentage was infected. The second striking fact from FIG. 8 was that an embodiment of C-PC-CDBN did not display the same qualitative behavior that D-PCCDBN displayed, and performed much worse. This is in line with previous results which showed that the distributed embodiment of Naive-DBN slightly out-performed the centralized version. However, the difference there was relatively minor, and the general trend for scaling up was qualitatively similar.

Figure 9:
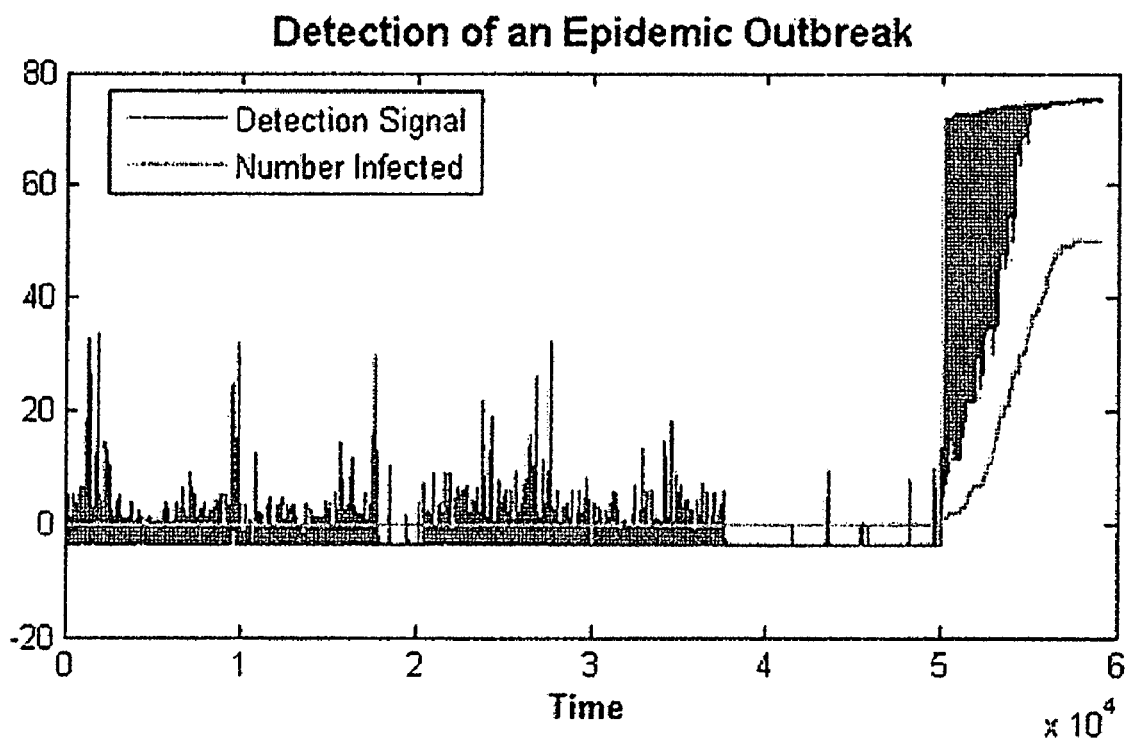
FIG. 9 shows a graph for the detection of an epidemic outbreak comparing an embodiment of a detection signal of the model and a number of infected hosts.

Further results are shown in FIG. 9. The goal of epidemic outbreak detection is to generate a large enough detection signal before a significant fraction of the population gets infected The graph of FIG. 9 shows an infection spreading through a population of 50 computer hosts using data from the corporation enterprise over 5 weeks. At time 50,000 a worm is introduced in the system and begins to spread. The intermediate spikes in the detection signal during periods of non-infection are due to diurnal cycles of activity, causing the signal to increase during the high-traffic workday periods. As can be seen from the graph, the detection signal spikes significantly after the infection begins.

Finally, PCCDBNs have been tested on the task of detecting a worm outbreak in a computer network and it has been shown that when the calculation is distributed in a particular manner, the detection results are qualitatively better than other cutting edge techniques, allowing detection (at less than 1 false positive per week) when a fixed absolute number of hosts are infected rather than when a fixed percentage is infected. The qualitative difference does not seem to hold when PCCDBNs are used in a centralized manner, reaffirming the previous findings that distributed detection can actually perform better than centralized detection, despite the fact that the centralized detector has available all information; whereas no single distributed detector has that information.

What is claimed is:

1. A method for determining a probability of a hidden variable from an observed variable in a Dynamic Bayesian Network, comprising:
   a) identifying the network based on predetermined criteria;
   b) determining a number of hidden variables in a time slice of the network;
   c) determining a number of said time slices of the network; wherein said predetermined criteria comprises determining if said time slice includes:
      an instantaneous causal chain of binary hidden variables; and
      determining if each of said binary hidden variables exhibit persistence in its on state; and
   d) determining the probability of the hidden variable from the observed variable in less than exponential time with respect to said number of hidden variables.

2. The method of claim 1, wherein said predetermined criteria comprises determining if said slice further includes:
   a) a binary observed variable; and
   b) said observed variable causally connected to one of said binary hidden variables.

3. The method of claim 2, wherein said predetermined criteria comprises determining if each of said binary bidden variables have a conditional distribution independent of time given a parent set of said binary hidden variable.

4. The method of claim 1, wherein the hidden variable is an attack on a host from an epidemic outbreak and the observed variable is an observation of said host.

5. The method of claim 4, wherein said attack is a worm attack.

6. The method of claim 4, wherein said observation is at least one of the set consisting of a number of packets sent by said host, a memory usage of said host, and a CPU usage of said host.

7. A device comprising a processor readable storage medium having instructions for a processor stored thereon that, when executed by the processor, result in determining a probability of a hidden variable from an observed variable in a Dynamic Bayesian Network, wherein said determining comprises:
   a) identifying the network based on predetermined criteria;
   b) determining a number of hidden variables in a time slice of the network;
   c) determining a number of said time slices of the network; wherein said predetermined criteria comprises determining if said time slice includes:
      an instantaneous causal chain of binary hidden variables; and
      determining if each of said binary hidden variables exhibit persistence in its on state; and
   d) determining the probability of the hidden variable from the observed variable in less than exponential time with respect to said number of hidden variables.

8. The device of claim 7, wherein said predetermined criteria comprises determining if said time slice further includes:
   a) a binary observed variable; and
   b) said observed variable causally connected to one of said binary hidden variables.

9. The device of claim 8, wherein said predetermined criteria comprises determining if each of said binary hidden variables have a conditional distribution independent of time given a parent set of said binary hidden variable.

10. The device of claim 8, wherein the hidden variable is an attack on a host from an epidemic outbreak and the observed variable is an observation of said host.

11. The device of claim 10, wherein said attack is a worm attack.

12. The device of claim 10, wherein said observation is at least one of the set consisting of: a number of packets sent by said host, a memory usage of said host, and a CPU usage of said host.

* * * * *